(12) United States Patent
Anderson

(10) Patent No.: US 11,344,593 B1
(45) Date of Patent: May 31, 2022

(54) CBD/THC/TERPENE CONSISTENT FORMULAS

(71) Applicant: Michael Anderson, Hillsboro Beach, FL (US)

(72) Inventor: Michael Anderson, Hillsboro Beach, FL (US)

( * ) Notice: Subject to any disclaimer, the term of this patent is extended or adjusted under 35 U.S.C. 154(b) by 128 days.

(21) Appl. No.: 16/997,515

(22) Filed: Aug. 19, 2020

Related U.S. Application Data

(60) Provisional application No. 62/888,985, filed on Aug. 19, 2019.

(51) Int. Cl.
| | | |
|---|---|---|
| *A61K 36/00* | (2006.01) | |
| *A61K 36/185* | (2006.01) | |
| *A61K 31/05* | (2006.01) | |
| *A61K 9/48* | (2006.01) | |
| *A61K 31/352* | (2006.01) | |

(52) U.S. Cl.
CPC .......... *A61K 36/185* (2013.01); *A61K 9/4891* (2013.01); *A61K 31/05* (2013.01); *A61K 31/352* (2013.01); *A61K 2236/30* (2013.01)

(58) Field of Classification Search
None
See application file for complete search history.

(56) References Cited

U.S. PATENT DOCUMENTS 9,095,554 B2 * 8/2015 Lewis .................... A01H 4/008
9,554,586 B2 1/2017 Sexton et al.

\* cited by examiner

*Primary Examiner* — Michael V Meller
(74) *Attorney, Agent, or Firm* — Malin Haley DiMaggio & Bowen, P.A.

(57) ABSTRACT

A method to produce a consistent product batch of cannabis and hemp plant active ingredients by isolating and separating the cannabis and hemp plant ingredients in prior processes and recombining the isolated ingredients in specify amounts for the final product. Encapsulating active ingredients together at different body internal release times to even out the active ingredient effects on the body over a time period to reduce highs and lows.

1 Claim, 5 Drawing Sheets

|  | THC | CBD | CBG | CBN | CBC | THCv | CBGa | CGCa | CBCa | THCa | CBDa |
|---|---|---|---|---|---|---|---|---|---|---|---|
| Relieves pain / Analgesic | ○ | ○ |  | ○ | ○ |  | ○ |  |  |  |  |
| Suppresses appetite/Helps with weight loss / Anorectic |  |  |  |  |  | ○ |  |  |  |  |  |
| Kills or slows bacteria growth / Antibacterial |  | ○ | ○ |  |  |  |  |  | ○ |  |  |
| Reduces blood sugar levels / Anti-diabetic |  | ○ |  |  |  |  |  |  |  |  |  |
| Reduces vomiting and nausea / Anti-emetic | ○ | ○ |  |  |  |  |  |  |  |  |  |
| Reduces seizures and convulsion / Anti-epileptic |  | ○ |  |  |  | ○ |  |  |  |  |  |
| Treats fungal Infection / Antifungal |  |  |  |  |  |  |  |  | ○ |  |  |
| Reduces Inflammation / Anti-inflammatory |  | ○ | ○ |  | ○ |  | ○ | ○ |  | ○ | ○ |
| Aids sleep / Anti-insomnia |  |  |  | ○ |  |  |  |  |  |  |  |
| Reduces risk of artery blockage / Anti-ischemic |  | ○ |  |  |  |  |  |  |  |  |  |
| Inhibits cell growth in tumors/cancer calls / Anti-proliferative |  | ○ | ○ |  | ○ |  |  |  |  | ○ | ○ |
| Treats psoriasis / Anti-psoriatic |  | ○ |  |  |  |  |  |  |  |  |  |
| Tranquilizing, used to manage psychosis / Antipsychotic |  | ○ |  |  |  |  |  |  |  |  |  |
| Suppresses muscle spasms / Antispasmodic | ○ | ○ |  | ○ |  |  |  |  |  | ○ |  |
| Relieves anxiety / Anxiolitic |  | ○ |  |  |  |  |  |  |  |  |  |
| Simulates appetite / Appetite Stimulant | ○ |  |  |  |  |  |  |  |  |  |  |
| Promotes bone growth / Bone Stimulant |  | ○ | ○ |  | ○ | ○ |  |  |  |  |  |
| Reduces function In the immune system / Immunosuppressive |  | ○ |  |  |  |  |  |  |  |  |  |
| Reduces contractions in the small intestines / Intestinal Anti-prokinetic |  | ○ |  |  |  |  |  |  |  |  |  |
| Protects nervous system degeneration / Neuroprotective |  | ○ |  |  |  |  |  |  |  |  |  |

FIG. 4

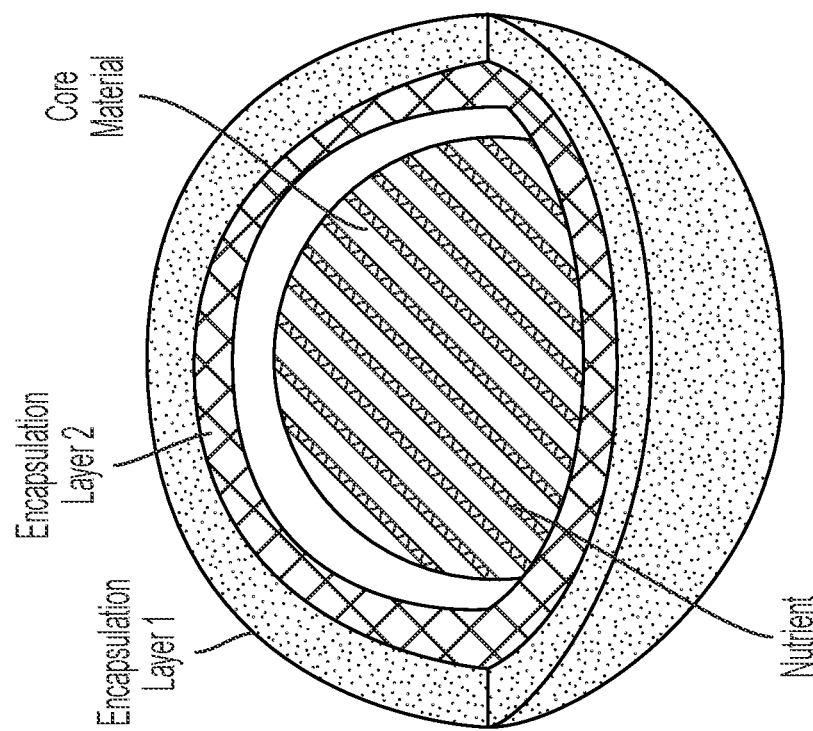
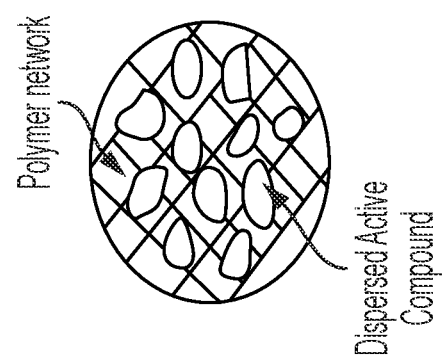
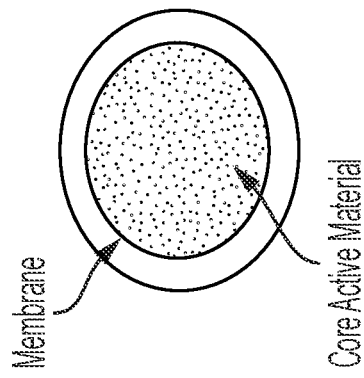
FIG. 5

CBD/THC/TERPENE CONSISTENT FORMULAS

CROSS REFERENCE TO RELATED APPLICATIONS

This application is based on provisional patent application filed Aug. 20, 2019 Ser. No. 62/888,985

FEDERALLY SPONSORED RESEARCH

None.

BACKGROUND OF THE INVENTION

1. Field of the Invention

This invention relates to a method for separation and isolation of the active components that come from the cannabis and/or hemp plant that provides for consistent product batches of active components when combined to specifically formulate the exact amount of each ingredient for a final product.

2. Related Prior Art

A large majority of CBD and or THC products manufactured ranging from pain cream, acne gels, tinctures, capsules, sprays, vapes, candies, shatter (butane hash oil), chocolates, tonics and gummy bears, just to name a few, use and isolate just the CBD molecule and does not contain any other THC or other CBD compounds such as CBDA, CBGA, CBG, CBN and so on, further described more in depth, in this invention, just pure isolated CBD, ranging in purity from 92 percent to 99 plus percent. It is semi-easy to deal with as there is no THC or other compounds and usually is much less expensive. Most chemists, scientists, formulators and manufacturers, including those who are in the business, know that full spectrum and broad spectrum CBD, with or without a portion being THC, is more valuable and diverse than just the CBD alone and has many more benefits.

Besides the higher cost, in full or broad spectrum, with or without THC, is the problem of having a consistent product, batch after batch. It is virtually impossible to extract the oil and have the oil the same every time; the result is the CBD is not marketable to large companies, as each batch is not the same, which means that every formula can deviate greatly and cannot not be an effective or reliable dose.

The present invention completely eliminates any variables that are found in today's concerns of percentages of different compounds/ingredients in a full and or broad spectrum of more than one ingredient and compound found in the plant of cannabis and hemp. This invention is not limited to the cannabis or hemp species, as the same can be applied for any other species of living or nonliving commodities and or products. Below here within is a further explanation of the invention.

SUMMARY OF THE INVENTION

This invention relates to a method to produce consistent product batches for a final product that is based on active ingredients and compounds that come from the cannabis and/or hemp plant. There are compounds found in the plants that include, but are not limited to, CBD, cannabigerol (CBG), CBG, CBC, CB1, Cannabinol (CBN), THC, THCA, CBA, CBA, THCV, delta-9-Tetrahydrocannabinol (THC), delta-8-Tetrahydrocannabinol, Cannabidiol (CBD), tetrahydrocannabinovarin (THCV), cannabidivarin (CBDV), and cannabichromene (CBC) and, also including the terpenes from the plants and extracted oils as well as other compounds, some as shown in some figures provided herein but not limited to.

Terpenes and terpenoids are compounds that are in the cannabis plant. There has been reportedly over 80 to over 200 or more terpenes that cannabis plants can produce and can vary greatly, depending on the strains, soil conditions, age, water/moisture amounts and sunlight and strains and genetics. There are over 80 cannabinoids in certain species of plants; so the compounds can be vast, which is another critical reason for this invention.

It is impossible to have consistency of more than one compound, without adding each separate compound/ingredient(s) to a formula, to make the compound a standard or constant exact dose for mass production of a drug or nutritional product. By adding each compound or ingredient(s), individually, consistency results on each batch produced for assured quality.

The process and manufacturing of the separated, individual compounds depends on converting, as an example, CBDA or THCA to CBD or THC that is done, by heat or not, and depending on the extraction or manufacturing process, that consist of heat variables or not. When heated, the conversion happens, but both separately are important to a body in their own ways. Terpenes are also very important molecules that can be used by heat conversion in both ways as well. Whether it is CBD, THC or Terpene family, every time separately manufactured/extracted or in different ratios, thus not allowing for the same product.

Taking the ingredients as mentioned herein, and others if ingredients that are separated, then mixed according to ratios or by weight to a predetermined formula and manufacturing process, the exact same full or broad spectrum CBD, THC and Terpene formula heated and no heated depending on what you want in the finished formula, can be created. Now consistent formulas can be created with over a 99 percent or higher ratio and be able to formulate many specific formulas in any combination of the above mentioned ingredients, including adding other nutritional and or pharmaceutical ingredients.

There are many ailments and health disorders and diseases that CBD, Terpenes and THC help treat and now can be specifically formulated for the exact amount of each ingredient required for a final product, whether for humans or animals, for ingesting, injections, or topical products for example, but not limited to, that help treat Parkinson, Alzheimer's, Seizures, Pain and inflammation to mention a few.

CBD, THC, Terpenes and other family of compounds found in cannabis and hemp plants and its family of plants has been shown to help in diseases and symptoms such as anxiety, psoriasis, cancer, MS, nausea, chronic pain, seizures/epilepsy, anxiety, psoriasis, diabetes, PTSD, strokes just to mention a few that includes THC and compounds as well as terpenes and their compounds.

It is an object of this invention to provide a method of producing consistent formulas of active ingredients from cannabis and hemp plants and Terpenes for consistent product batches when combined of CBD, THC and Terpenes when combined to formulate specific ingredients in a final product.

BRIEF DESCRIPTION OF THE DRAWINGS

FIG. 4 shows Terpene health benefits.
FIG. 5 shows a cutaway diagram of encapsulated active ingredient.

DESCRIPTION OF PREFERRED EMBODIMENTS OF THE INVENTION

Figure 1:
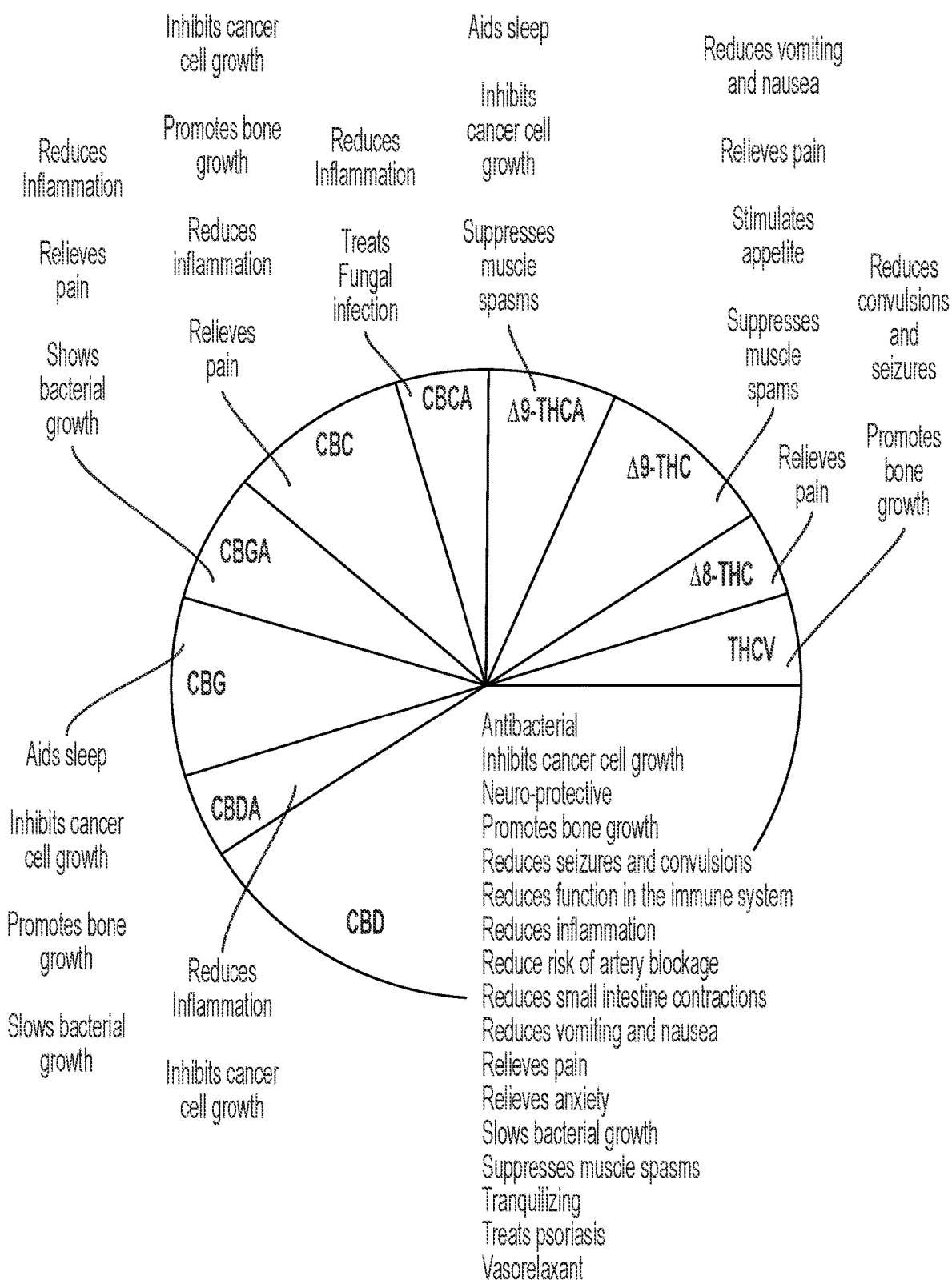
FIG. 1 shows a chart of CBD ingredients.
Figure 2:
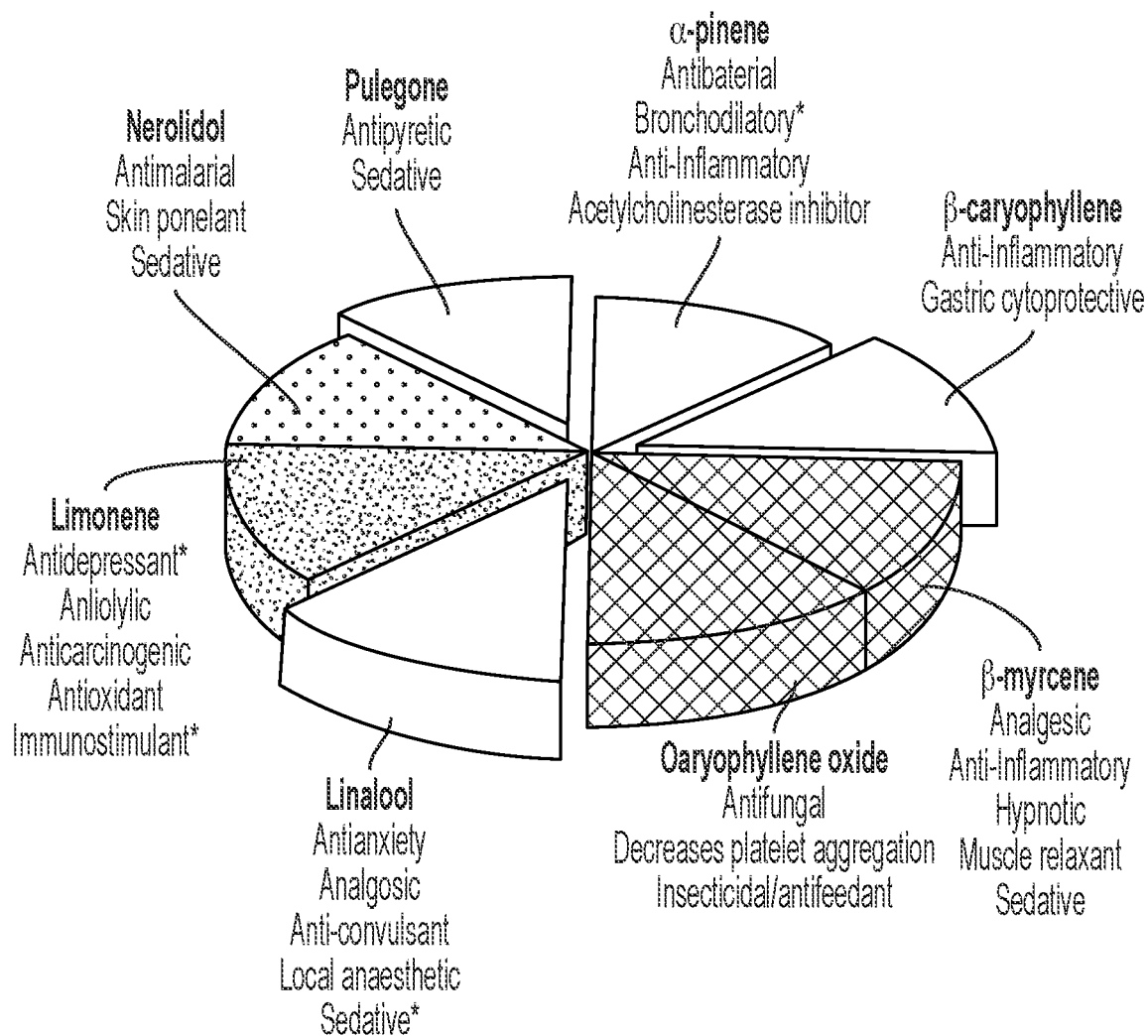
FIG. 2 shows a chart of a list of actions associated with Terpenes.
Figure 3:
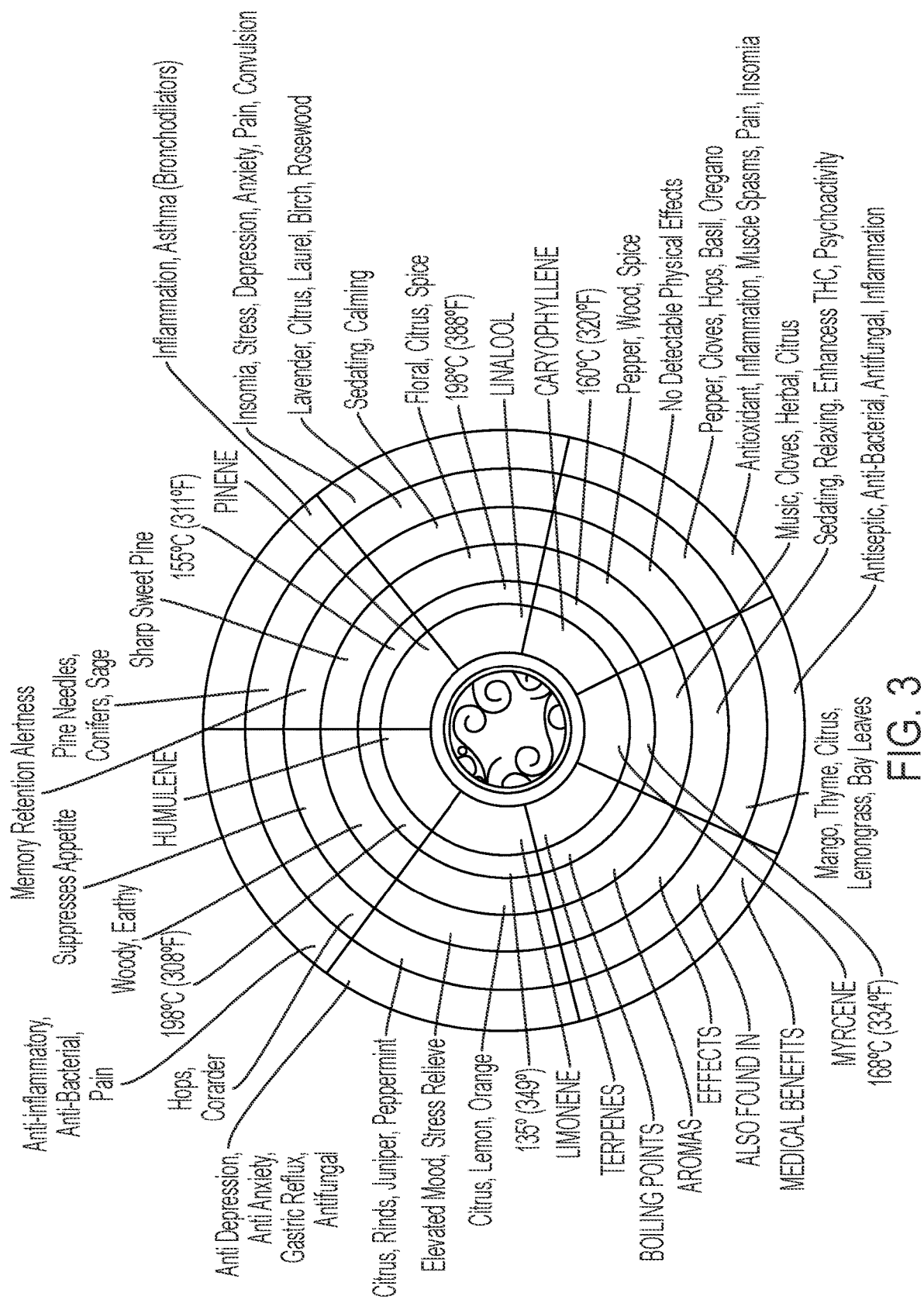
FIG. 3 shows a chart of medical benefits of Terpenes.

An example below for a formula, for end product consistency, add 1 milligram of each of the following previously isolated, separated components/compounds/ingredients in a prior separation/extraction process, to provide for the first time a consistent final product formula on an ongoing basis, without deviation and with complete consistency, including adding other drugs, medicines and or nutraceuticals of any kind. The following is only an example to show the invention is critical and cannot be done without the invention process, if a formula needed to be 1 milligram of each: cannabigerol (CBG), cannabichromene (CBC), cannabidiol (CBD), tetrahydrocannabinol (THC), cannabinol (CBN) and cannabinodiol (CBDL), cannabicyclol (CBL), cannabivarin (CBV), tetrahydrocannabivarin (THCV), cannabidivarin (CBDV), cannabichromevarin (CBCV), cannabigerovarin (CBGV), cannabigerol monomethyl ether (CBGM), cannabinerolic acid, cannabidiolic acid (CBDA), cannabinol propyl variant (CBNV), cannabitriol (CBO), tetrahydrocannabinolic acid (THCA), and tetrahydrocannabivarinic acid (THCVA) and terpenes such as: aromadendrene, bergamottin, bergamotol, bisabolene, borneol, 4-3-carene, caryophyllene, cineole/eucalyptol, p-cymene, dihydrojasmone, elemene, farnesene, fenchol, geranylacetate, guaiol, humulene, isopulegol, limonene, linalool, menthone, menthol, menthofuran, myrcene, nerylacetate, neomenthylacetate, ocimene, perillylalcohol, phellandrene, pinene, pulegone, sabinene, terpinene, terpineol, terpineol-4-ol, terpinolene, and derivatives, isomers, enantiomers.

Another embodiment of the present invention provides a time release/extended release composition comprising certain ingredients that can be provided that are from Evonics and Colorcon among other companies, ingredients that can provide coating materials, including other ingredients that can be used in itself or part of such as dextrin's, starch and chitosan.

Thereof one or more nutra and/or pharma excipients that are for multi hour release of active materials instead of all at once. Manufacturing can be done in a coating pan, fluid beds, among other type of spray drying techniques to provide a controlled release pattern that can be layered with multiple coatings and multiple coating ingredients, depending on the release of what is desired, to protect against moisture, to help in odor and taste reduction, and to making oil into water soluble products.

Furthermore, specific coating materials can be used so that certain active ingredient(s) will only dissolve/enter into the blood stream in specific areas of the body such as stomach, large intestine, duodenum and ileum. With this technique with certain minerals, vitamins, herbs and or drugs, the amount of actives used can be much less than a standard dose due to releasing, specifically including time release over time, of the active ingredient(s). There are many formulas that can be done by this invention, and below are some examples, but are not limited to the examples, as there are limitless combinations that now can be done based on this invention.

Encapsulation Example 1

100 mg caffeine, 100 mg taurine, 20 mg niacin, 50 mg potassium, 5 mg magnesium, 1 mg CBD, 1 mg THC, 1 mg THCA, 1 mg CBG and 30 mg of calcium every hour over a period of 7 hours.

Encapsulation Example 2

2 mg melatonin, 30 mg valerian root, 35 mg 1-tryptophan, 15 mg gaba, 1 mg CBD, 1 mg THC, 1 mg THCA, 1 mg CBG.

Encapsulation Example 3 mg of CBD, either isolate, full spectrum or broad spectrum, 1 mg CBD, 1 mg THC, 1 mg THCA, 1 mg CBG and or any amounts of terpenes or any single or any combination thereof, release every hour on the hour for a period of 8 hours or any amount of hours desired.

With this invention there are unlimited amounts of new medicines that are manmade/synthetic or by nature that have enormous applications to the body and market. Having ingredients release overtime is the most efficient way of obtaining the highest bioavailability possible to any human or animal.

Furthermore the ingredients/compounds can be microencapsulated for specific time release, targeted release, making water soluble oil to odor and taste masking that can be crucial for specific formulas.

The invention claimed is:
1. A method of treating Alzheimer's disease in a human in need thereof consisting essentially of administering to said human in need thereof an extended release capsule consisting essentially of therapeutically effective amounts of isolated THC, isolated CBD, valerian root, gaba, caffeine, and melatonin to effectively treat the Alzheimer's in said human in need thereof.

* * * * *